United States Patent
Gottelt

[11] 3,952,581
[45] Apr. 27, 1976

[54] ULTRASONIC FLAW DETECTING APPARATUS FOR TURBINE ROTORS

[75] Inventor: Herbert R. Gottelt, Mount Prospect, Ill.

[73] Assignee: Alco Standard Corporation, Valley Forge, Pa.

[22] Filed: Nov. 29, 1974

[21] Appl. No.: 528,586

[52] U.S. Cl. .............................................. 73/67.8 S
[51] Int. Cl.² ........................................ G01N 29/04
[58] Field of Search............ 73/67.8 R, 67.8 S, 67.9, 73/71.5 US, 1 DV; 250/360; 324/37

[56] References Cited
UNITED STATES PATENTS

| | | | |
|---|---|---|---|
| 3,111,027 | 11/1963 | Moffatt et al...................... | 73/67.8 S |
| 3,780,571 | 12/1973 | Wiesener.......................... | 73/67.8 S |
| 3,809,607 | 5/1974 | Murray et al.................... | 73/67.8 S X |

FOREIGN PATENTS OR APPLICATIONS 1,600,873   9/1970   France.............................. 73/67.8 S

*Primary Examiner*—Richard C. Queisser
*Assistant Examiner*—John P. Beauchamp
*Attorney, Agent, or Firm*—Haight, Hofeldt, Davis & Jambor

[57] ABSTRACT

A flaw detecting apparatus is insertable into the bore of a rotor being tested. A chamber is formed by a structure mounted on the rotor in a cantilever fashion. The chamber provides an area in which the test unit may be checked and worked on. Calibration blocks are located in the chamber to calibrate the amplitude and distance signals for both axial and rotational modes of ultrasonic propagation. A motor mount at the outward end is pivoted to provide ready access to the chamber.

9 Claims, 10 Drawing Figures

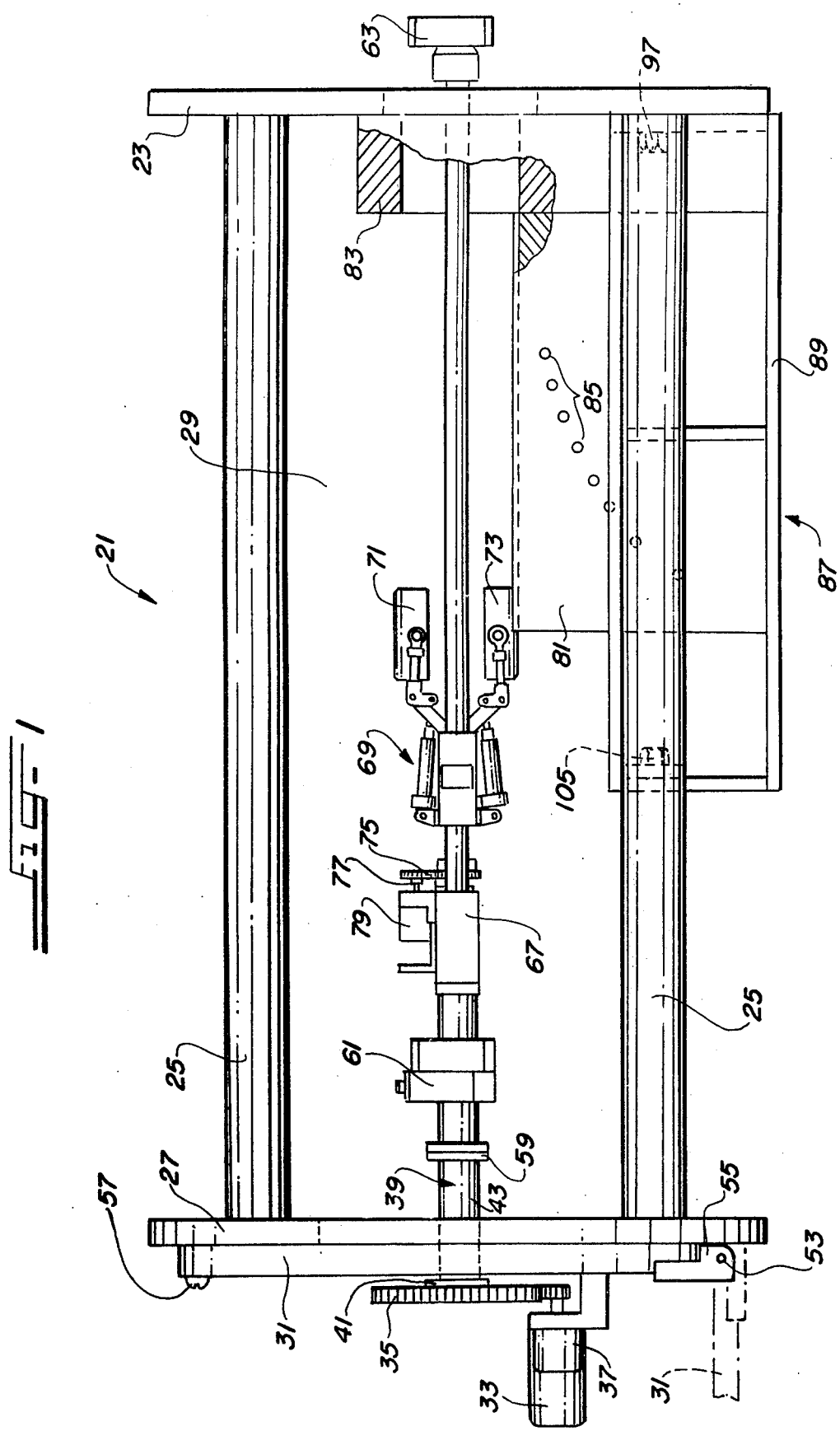

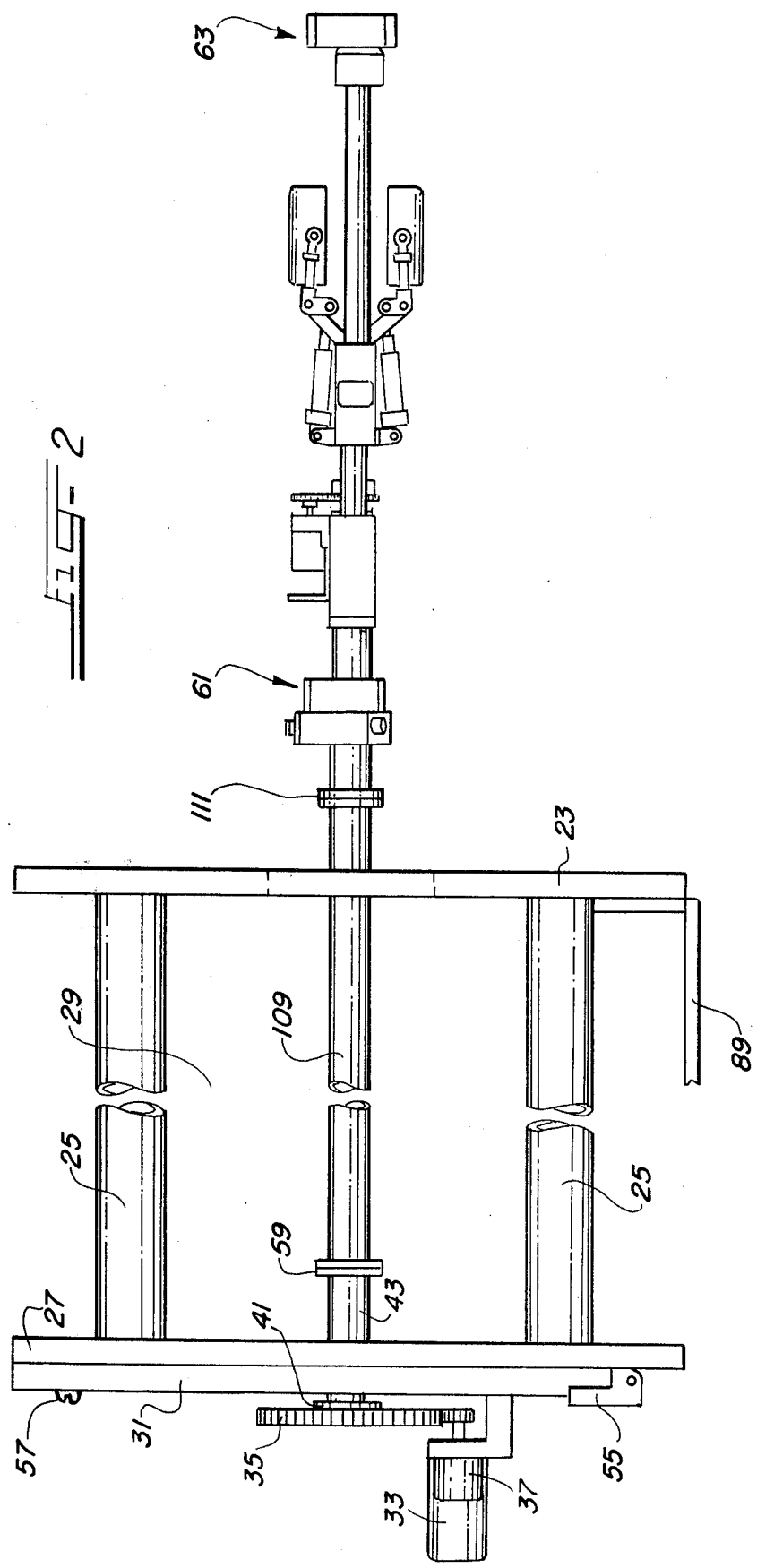

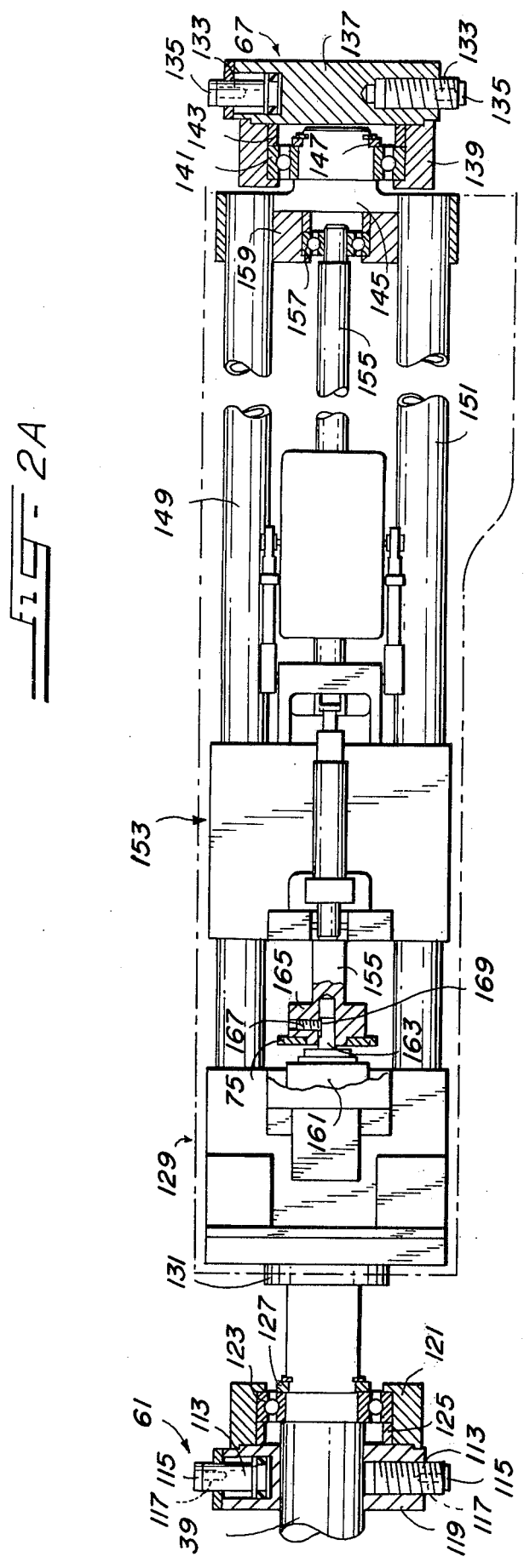

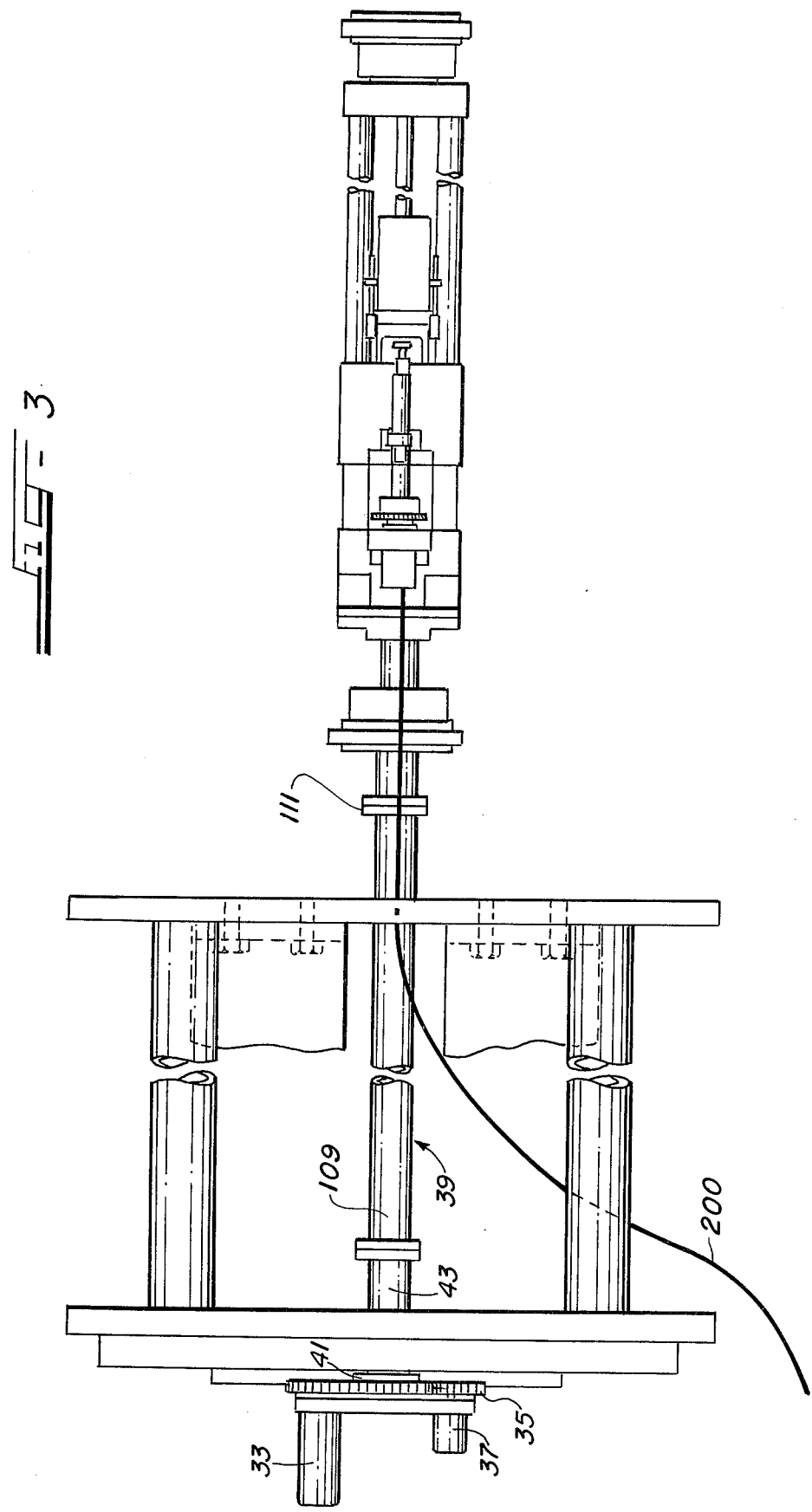

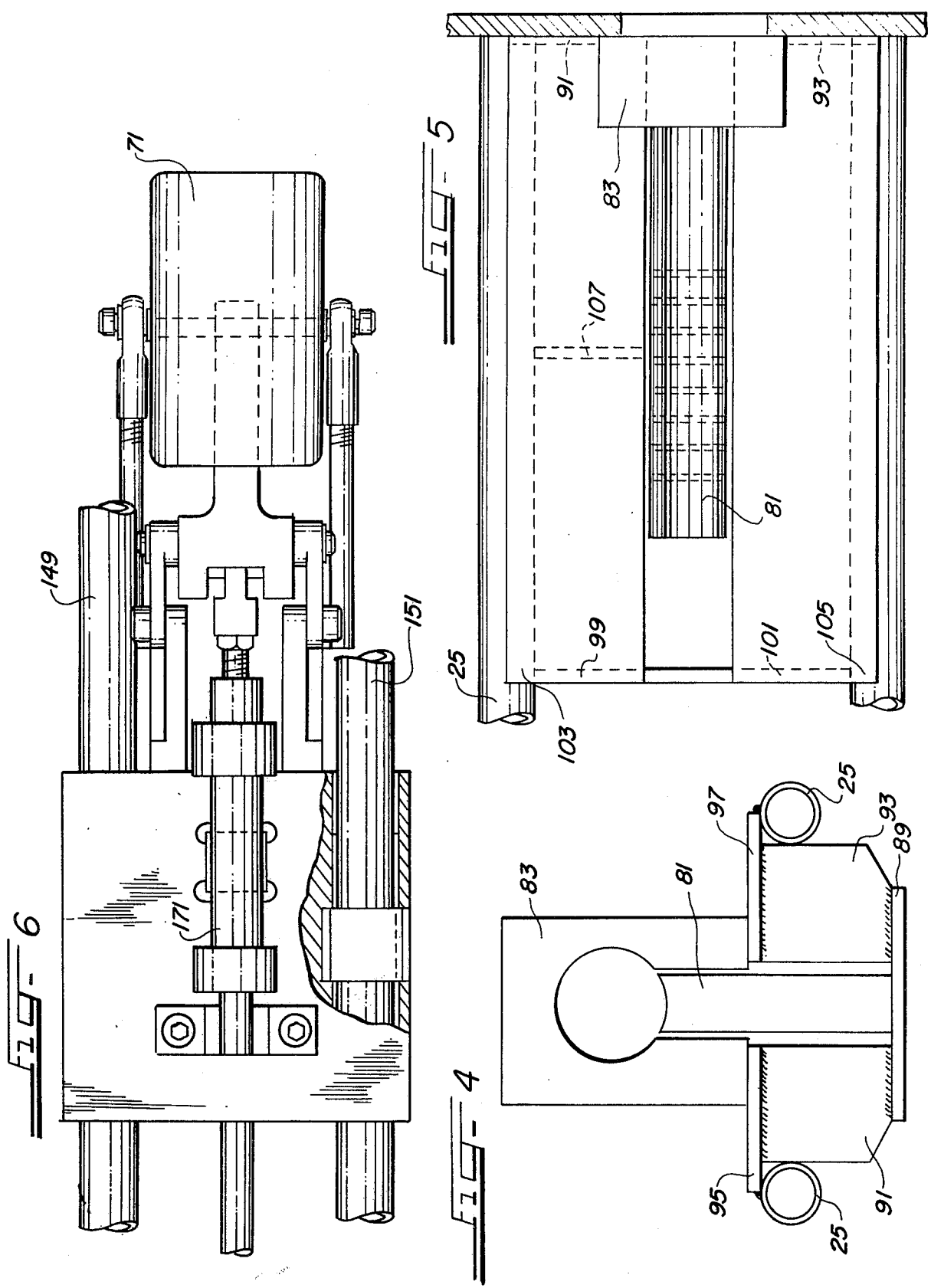

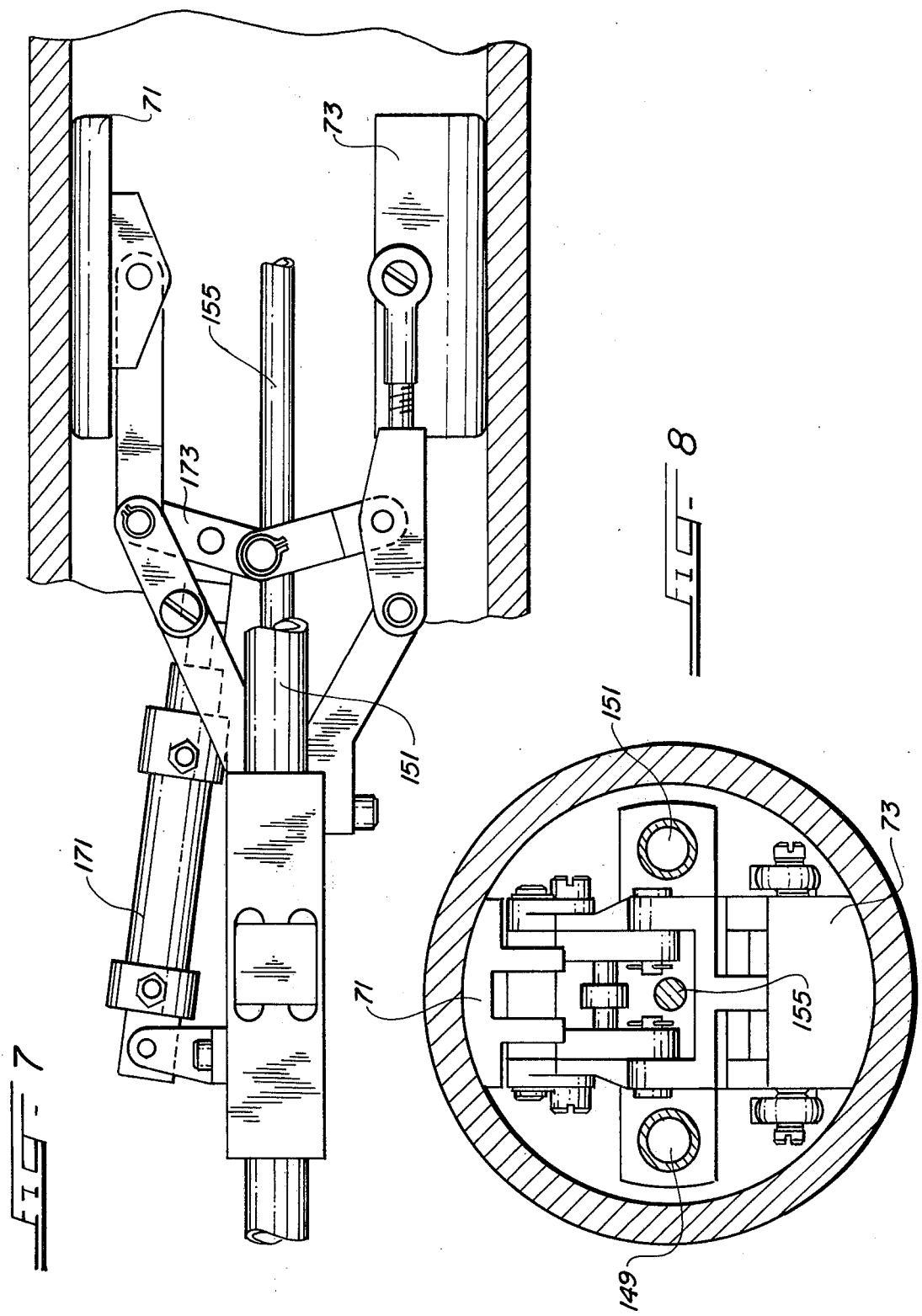

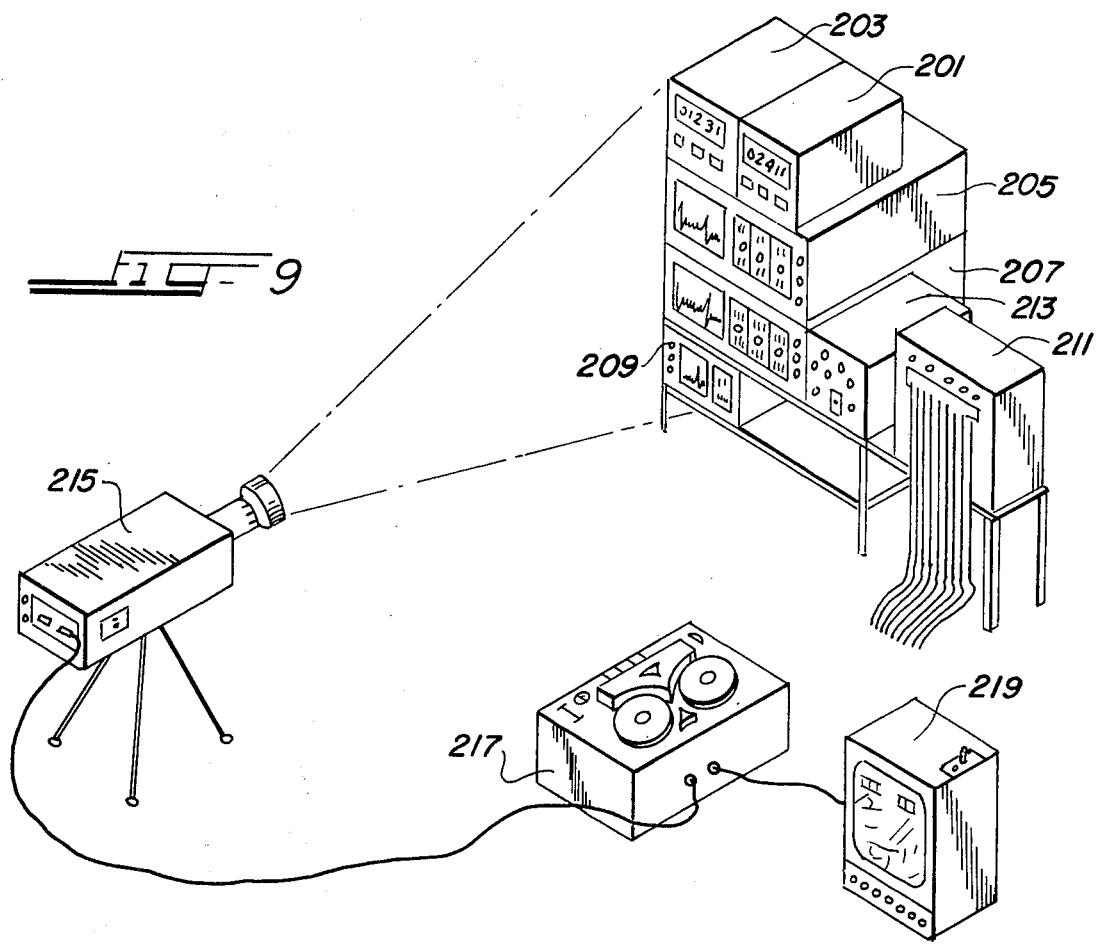

ULTRASONIC FLAW DETECTING APPARATUS FOR TURBINE ROTORS

BACKGROUND OF THE INVENTION

1. Field of the Invention

This invention relates generally to a flaw detecting apparatus insertable into the bore of a rotor, and more specifically, this invention relates to a cantilever support arrangement that permits a flaw detecting apparatus to be worked upon and calibrated with ease.

2. Description of the Prior Art

This invention is an improvement of the basic flaw testing apparatus shown and described in the copending application of Robert D. Smith entitled "NON-DESTRUCTIVE TEST APPARATUS AND METHOD FOR A MATERIAL HAVING A CAVITY THEREIN", U.S. patent application Ser. No. 421,131, filed Dec. 3, 1973, and assigned to the same assignee as the present application. The disclosure of this application is expressly incorporated herein by reference. As pointed out in that application, the non-destructive ultrasonic testing approach disclosed therein offers many advantages over prior art flaw detecting approaches. While the system disclosed in that application provides a desirable solution to the flaw testing problems of the prior art, the necessity of removing the shield or mounting plate to add extensions, and of having to completely remove the test apparatus from the bore to work on it, added undesirable difficulties to the operation. Further, calibration of the apparatus was difficult. Accordingly, it is desirable to have an ultrasonic flaw testing apparatus that could simplify the use of extension sections and would permit calibration of the system. Further, it is desirable to be able to work on the apparatus in an area where its operation can be checked without having to continually insert and remove the apparatus from the rotor bore.

SUMMARY OF THE INVENTION

The present invention provides all the advantages of the system in the aforesaid U.S. patent application Ser. No. 421,131, and improves thereupon by providing an arrangement by which the test unit can be relatively easily reached for work thereon while it is in a test status, thus permitting any defective operation to be readily observed, as well as the results of any repair or maintenance procedures. In addition, this improved arrangement utilizes a calibration system that can be left in place so that the apparatus can be easily recalibrated during operation, if any question as to the calibration arises.

To achieve these desired results, the present invention employs a cantilever support structure in which a first or primary mounting plate is securely affixed to the rotor being tested. This primary mounting plate has an opening therein which is aligned with the bore of the rotor being tested, in order that a test unit can be inserted into the bore through the opening. A supporting arrangement, such as a series of supporting rods, extends outwardly from the primary mounting plate to support a motor mounting plate in a cantilever fashion. In a preferred embodiment, the supporting rods actually rigidly support a support ring to which the motor mounting plate is attached, such as by a hinge connection.

A chamber is defined by the primary mounting plate, the supporting rods, and the support ring and/or the motor mounting plate. This chamber provides an area in which an ultrasonic test unit may be located for calibration, repair or testing. Access to the chamber may be readily achieved through the spaces between the supporting rods, as well as through the support ring when the motor mounting plate is pivoted away from the support ring.

On the motor mounting plate there is a drive motor that is utilized to drive the test unit in the rotary scan. As described in the aforesaid U.S. patent application Ser. No. 421,131, the entire test unit is rotated by this drive, while an axial sweep is achieved by a movable carriage having a drive arrangement integral with the test unit. The drive motor on the motor mounting plate is connected to a short section of drive shaft, which is then coupled either directly to the test unit or extension sections of drive shaft. The short section of drive shaft is sufficiently short to clear the support ring when the motor mounting plate is pivoted away from the support ring about the hinge attachment. With this arrangement an additional benefit is obtained by having the coupling and uncoupling of extension sections of drive shaft take place in the chamber, which obviates the necessity of removing the primary mounting plate to gain access to the coupling device.

Calibration blocks are located in the chamber to calibrate the ultrasonic apparatus. One calibration block is for calibrating the axial scan, while another block is for calibrating the rotational scan. (It should be understood that while reference is made to two separate calibration blocks, a single block permitting calibration of both type of scan would be equally satisfactory.) These blocks are removably mounted in a structure in the chamber, with the axial calibration block extending from the primary mounting plate along the drive shaft axis, while the rotational calibration block is located adjacent the opening in the primary mounting plate. Each of the calibration blocks has a surface corresponding to the surface of the bore for the type of scan being calibrated, and each has a series of flaw duplicating holes formed therein in a known distribution to permit accurate calibration of the equipment. For the calibration procedure, the test unit is coupled directly to the short section of drive shaft connected to the motor on the motor mounting plate. This same positioning of the test unit is utilized for the first scan of the bore. Subsequent scans are realized by inserting extensions of precise length between the short section of drive shaft connected to the motor and the test unit.

The test unit has spider structures adjacent each end thereof for supporting the structure in the bore. In the calibration position the spider adjacent the motor drive shaft end will not provide any support, although a suitable pad arrangement could be provided in the chamber, if desired. A movable carriage is driven in an axial sweep by a motor and lead screw arrangement along a pair of slide rails. The movable carriage bears a pair of ultrasonic transducer transporting shoes which are biased against the wall of the bore. A proper couplant is placed between the shoes and the wall of the bore.

The axial and circumferential or rotational position of the test device is determined by indexing and encoding apparatus which transmit electrical signals indicative of these parameters. These signals, as well as the output signals of the transducers, are conveyed to appropriate decoding and storing devices, where the information is visually displayed, analyzed and stored for future analysis and reference.

These and other objects, advantages and features of this invention will hereinafter appear, and for purposes of illustration, but not of limitation, an exemplary embodiment of the subject invention is shown in the appended drawing.

BRIEF DESCRIPTION OF THE DRAWING

FIG. 1 is a side elevational view illustrating a preferred embodiment of the subject invention with the test unit in the calibration chamber.

FIG. 2 is a side elevational view of the preferred embodiment of the subject invention with the test unit shown in the position it would take when inserted into the bore of a rotor for testing.

FIG. 2A is an enlarged view of the test unit of FIG. 2.

FIG. 3 is a top plan view of the embodiment of FIG. 2.

FIG. 4 is a partial cross-sectional view of the calibration block structure in FIG. 1 when looking from left to right in that figure.

FIG. 5 is a partial top plan view of the calibrating block structure of FIG. 2.

FIG. 6 is an enlarged top plan view of the movable carriage of the test device illustrating a slight modification in the shoe biasing structure.

FIG. 7 is a side elevational view of the structure in FIG. 6 located in the bore of a rotor.

FIG. 8 is a left end elevational view of the structure in FIG. 7.

FIG. 9 is a schematic illustration of the decoding, display and storage equipment utilized in this preferred embodiment of the subject invention.

DETAILED DESCRIPTION OF THE PREFERRED EMBODIMENT

With respect to the drawing, FIG. 1 illustrates an ultrasonic flaw detecting arrangement 21 for examining turbine motors. In this view the test device is shown in the retracted calibration or initial test position. A mounting plate 23 is firmly secured to the end of the rotor and has an opening formed therein through which the test unit will be inserted into the bore. Any appropriate type of solid mounting may be utilized for plate 23, such as the bolt 71, 73 and 75 shown in the aforementioned U.S. patent application Ser. No. 421,131.

A series of supporting rods or bars 25 extend from mounting plate 23 to annular support ring 27. Rods 25 are formed of any suitable strong material that can support the structure in the cantilever fashion as shown. In the case of this preferred embodiment, four such supporting rods 25 are utilized, two each in the horizontal planes represented by the two rods 25 that are visible in FIG. 1. The space between mounting plate 23 and support ring 27 may thus be thought of as a chamber 29 which is relatively easily accessible for work on the operative portions of the detecting apparatus 21, such as for any repairs or adjustments that may be necessary, as well as providing an area for calibration tests and adding extensions to the drive tube for the apparatus. In addition, this is the initial scan position for the apparatus.

A motor mounting plate 31 is connected to annular support ring 27. In some situations the plate 31 and ring 27 could be integral to form a single motor mounting plate, but in this preferred embodiment a separate motor mounting plate 31 is utilized.

A motor 33 is mounted on the plate 31 and, as shown in the aforementioned U.S. patent application Ser. No. 421,131, motor 33 drives a bull gear 35 through a pinion gear (not readily visible in FIG. 1). An indexing and encoding device 37 is driven from the bull gear 35, as shown in the aforementioned U.S. patent application Ser. No. 421,131. The indexing and encloding device 37 is responsive to the motion of the bull gear 35, as driven by motor 33, to index motion of the bull gear 35 from a given reference point and to produce coded electrical signals indicative of the positioning. Since the motor 33 drives the complete test unit in a rotary fashion when it is located within the bore of the rotor being tested (as described in U.S. Pat. application serial No. 421,131), the signals from device 37 are utilized to accurately determine the rotational position of the apparatus.

Motor mounting plate 31 not only serves to mount the motor 33, indexing and encoding device 37, and the associated gearing, but it also serves to center the drive tube 39 and to provide a support bearing therefor. In this regard, a coupling or connecting flange 41 interconnects bull gear 35 and a relatively short section or portion 43 of a drive shaft or tube 39. Drive shaft or tube portion 43 rotates in a bearing (not shown), which is held in mounting plate 31. Portion 43 is releasably connected to the remainder of drive tube 39 in an suitable fashion for the transmission of rotary motion.

The main feature of drive shaft or tube section 43 is that it be short enough to pass through the ring 27 when the motor mounting plate 31 is pivoted away from the support ring 27. After disengagement of portion 43 from the rest of drive tube 39, the entire motor mounting plate 31 may be pivoted from the vertical to the horizontal position shown in phantom line about the pivot point 53. Pivot point 53 is actually a hinge rod which is part of the hinge structure 55 connected to the support ring 27. Motor mounting plate 31 is held in the vertical position by any suitable fastening device, such as a threaded bolt 57, as illustrated in FIG. 1. The advantage of having such a hinged support for the motor mounting plate 31 is that, when the plate 31 is moved to the horizontal position, access to the interior of chamber 29 is easily achieved to add extension lengths of drive shaft or tube 39, or to otherwise work with the detecting apparatus.

With reference now to the internal portion of chamber 29, it may be seen that a coupling device 59 is provided for adjoining sections of drive tube 39. This coupling device 59 may be any sort of arrangement by which two sections of drive tube 39 may be tightly connected. While in FIG. 1 the coupling device 59 is utilized directly to the drive tube connected to the test unit, during operation of the apparatus coupling devices of this nature will have to be utilized to insert extensions of the drive tube, as shown in FIGS. 2 and 3. As the precise designation of the location of flaws depends upon an accurate knowledge of the length of the drive tube 39, the main condition for the coupling device 59 is that it tightly connect sections of the drive tube, without distortion, in order that the total length of the drive tube can be known with great precision.

The length of the apparatus to the right of coupling device 59 in FIG. 1 is the section of the apparatus that includes the operative portions thereof and is referred to as the test unit (129 in FIG. 2A). This section or test unit includes a first spider arrangement 61 which is adapted to support the end of this section adjacent to the coupling device 59, while a second spider arrangement 63 supports the other end thereof. In this particular placement of the test unit, spider 63 is located in the bore of rotor being tested, while spider 61 is unsupported in chamber 29. If desired, a supporting pad arrangement representative of the bore could be utilized in chamber 29 to permit use of spider 61.

A drive assembly 67 includes a motor that drives a movable test carriage 69 in the axial direction via a lead screw arrangement. The test carriage 69 includes the test shoes 71 and 73, which carry the ultrasonic transducers. A gear 75 associated with the motor of drive unit 67 drives a gear 77 to cause an indexing and encoding device 79 to provide electrical output signals indicative of the axial position of the movable test carriage 69.

The unextended or work or calibration position of the test unit illustrated in FIG. 1 is utilized to test the first portion of bore beyond the mounting plate 23. In addition, this position is utilized to calibrate the testing device. To achieve this, a pair of calibrating blocks 81 and 83 are utilized. The calibration block 81 is utilized to calibrate the amplitude and distance for an axial mode wave instrumentation, while block 83 is utilized to calibrate the amplitude and distance for a circumferential or rotational mode wave. To achieve the calibration, a series of holes 85 are located at known points along the axial direction of block 81 and at known distances from the surface along which the test shoes 71 and 73 move. Of course, the size and nature of these holes are also known. Similar holes are located in the calibration block 83 for purposes of calibrating in the radial direction.

With reference now also to FIGS. 4 and 5, it may be seen that the calibration blocks 81 and 83 are mounted in a support frame 87 that has a continuous bottom portion 89. At mounting plate 23 there are vertical support sections or ears 91 and 93. Section 91 is welded by connection to one of the supporting rods 25 through flange 95, while section 93 is releasably connected to another supporting rod 25 by a bolt-in weldment 97. Use of the bolt-in weldment 97 permits insertion and removal of the calibration blocks 81 and 83. Similar supporting sections or ears 99 and 101 are located at the other end of frame 87, with section 99 having a permanent weld connection 103, while section 101 has a bolt-in weldment 105, for the same purpose as bolt-in weldment 97. Approximately halfway between support section 91 and 99, a third support section 107 is added, although there is not such section between support sections 93 and 101. With this arrangement, the calibration blocks 81 and 83 may be left in position during use of the operation, and yet they may be easily removed when it is so desired.

With reference now to FIGS. 2 and 3, the detecting apparatus may be seen as it appears when inserted into the bore of the rotor being tested. This is achieved by the addition of an extension drive tube 109, which extends from the coupling arrangement 59 to a coupling arrangement 111. Actually, coupling arrangements 59 and 111 both include a portion of the original coupling 59, but for ease of reference the coupling arrangement in chamber 29 will always be referred to as coupling 59, although only one-half of this coupling arrangement remains constant. Of course, it should be noted that additional extensions of the driving tube may be utilized to extend the testing apparatus further into the bore of the rotor.

The spider assembly 61 may be either a three or four-legged spider, as desired, and thus the spider 61 will have either three or four legs 113, one or more of which may be biased, such as by a pneumatic arrangement, to lock the spider in place. In order to prevent scratching of the bore, the legs 113 may have pads or feet 115 formed of a suitable relatively soft material, such as nylon, connected thereto. The pads or feet 115 may be attached by any appropriate manner, such as by a stem 117 inserted into the leg 113. The main body or housing 119 of the spider 61 is a generally annular cylindrical member with extending portions corresponding to legs 113 and having an opening therein for the drive shaft 39. A cylindrical annular extending arm 121 carries a bearing 123 to support the drive tube 39. A spacer 125 is utilized to separate the bearing 123 from the body 119 of the spider 61. In addition, a spacer 127 is utilized to secure the other side of the bearing and prevent flotation thereof. Thus, the spider 61 supports this end of the drive tube 39 and provides a bearing surface therefor.

The drive tube 39 is coupled to the test unit 129 by a coupler 131. As a result of the coupling 131, the rotational motion of the drive tube 39 is transmitted to the test unit 129 to cause this whole structure to rotate in the bore. The other end of the rotating measuring apparatus is supported by a spider 63, which may be a three-legged or four-legged spider having legs 133 with pads or feet 135. The body 137 of spider arrangement 63 has a annular projecting arm 139, which carries a bearing 141. Spacer 143 separates bearing 141 from the body 137. Bearing 141 supports a projecting shaft portion 145, and another spacer 147 is located on the projecting shaft portion 145 to prevent floating of the bearing.

The shaft portion 145 extends from an end section 150 of test unit 129. Test unit 129 includes a pair of slide rails 149 and 151, which are mounted in the end section 150. A carriage 153 (as this carriage differs slightly from the carriage 69 in FIG. 1, a new reference numeral has been utilized) moves along the slide rails 149 and 151 by means of a drive that includes a lead screw 155. Lead screw 155 is mounted for rotation in a bearing 157 in end section 150. A supporting spacer 159 is utilized in conjunction with bearing 157. The lead screw 155 mates with appropriate threads in the carriage 153 to move the carriage along the slide rails 149 and 151 when the lead screw is rotated.

Rotation of lead screw 155 is achieved by means of a motor 161 located in the drive assembly 67. The shaft 163 of motor 161 is connected to lead screw 155 in any appropriate manner, such as by utilization of a hub 165, which is shrunk on lead screw 155 to form a tight fit. A set screw 167 engages an appropriate groove 169 in the shaft 163 to provide the desired interconnection, which is yet separable. A gear wheel 75 is press fitted on a reduced portion of hub 165 to drive the indexing and encoding device 79 through the spur gear 77. The indexing and encoding device 79 produces an electrical pulse for each one thousandth of an inch of axial motion of the carriage 153, so that the precise axial location of the carriage 153 may be accurately determined.

Carriage 153, which differs slightly from the carriage 69 illustrated in FIG. 1, is also illustrated in greater detail in FIGS. 6, 7 and 8. As indicated in the aforesaid U.S. patent application Ser. No. 421,131, the transducer shoes 71 and 73 would be of some material such as plexiglass and would carry one or more ultrasonic transducers. As may be seen especially well in FIG. 7, the shoes 71 and 73 will vary in size depending upon the mode of ultrasonic waves utilized and the number of transducers in a particular shoe. The shoes 71 and 73 are pneumatically biased against the circumference of the bore by a pneumatic arrangement 171. Pneumatic arrangement 171 acts through a linkage 173 to simultaneously bias the shoes 71 and 73 against the circumference of the bore by means of a single pneumatic activator, as opposed to the two distinct pneumatic biasing arrangements utilized in the embodiments of FIGS. 1 and 2.

With reference now to FIG. 9, an arrangement for displaying and analyzing the results of the testing apparatus are disclosed. Motor control and position readout devices 201 and 203 are responsive to the indexing and encoding devices 37 and 79 to provide a count output that indicates the precise axial and rotational location of the test unit in the rotor portion being tested. Ultrasonic testing instruments 205, 207 and 209 provide visual displays of the signals produced by the reflection of ultrasonic signals. These displays are essentially the same as those produced by sonar equipment. The outputs from these various devices are fed to a brush strip chart recorder 211, which records the signals indicating the position of the test unit and signals indicating whether a flaw has been detected at that point.

While not directly related to the display and analysis of the test results, a controller 213 that is utilized in regulating the pneumatic and liquid coupling supply is included with these instruments. It should be noted, as schematically illustated in FIG. 3, that the pneumatic actuating gas (air) and the couplant, as well as electrical power and signal transmitting capabilities have to be conveyed to test unit 129. A flexible cable 200 serves to encapsulate these transmitting lines. Cable 200 passes through chamber 29, the opening in mounting plate 23 (which is larger than drive shaft 39), the openings between legs 113 of spider 61, to the test unit 129.

The visual outputs of the devices 201, 203, 205, 207 and 209 are scanned by a television camera 215 to produce images that may be recorded for later analysis. The output of television camera 215 is conveyed to a monitor 217, which displays the pickup of television camera 215 for the purpose of checking the signals produced by the camera. In addition, the monitor 217 has the advantage that another party can also be observing the output of the testing instruments at a distance from the location where the camera 215 and the instruments are located. Finally, the output of the monitor is conveyed to a recording device 219 in order that the signals of the television camera 215 may be permanently recorded for future observation and analysis.

It should be understood that various modifications, changes and variations may be made in the arrangements, operations and details of construction of the elements disclosed herein without departing from the spirit and scope of this invention.

I claim:

1. An ultrasonic flaw detecting arrangement for rotor bores comprising:
    a primary mounting plate secured to the rotor and having a central opening therein permitting access to the bore of the rotor;
    a motor mounting plate spaced from said primary mounting plate;
    supporting means extending between said mounting plates to rigidly support said motor mounting plate on said primary mounting plate in a cantilever fashion;
    a chamber defined by said mounting plates and said supporting means, said supporting means being a plurality of spaced extending members so that said chamber is accessible to an operator;
    an ultrasonic test unit insertable into the bore of the rotor, said test unit being positionable in said chamber for inspection and servicing while said primary mounting plate remains secured to the rotor; and
    a motor mounted on said motor mounting plate to actuate a drive shaft for said test unit.

2. An arrangement as claimed in claim 1 and further comprising a support ring at the end of said supporting means away from said primary mounting plate, said motor mounting plate being pivotably mounted on said support ring to permit ease of access to said chamber.

3. An ultrasonic flaw detecting arrangement for rotor bores comprising:
    a primary mounting plate secured to the rotor and having a central opening therein permitting access to the bore of the rotor;
    a motor mounting plate spaced from said primary mounting plate;
    supporting means extending between said mounting plates to rigidly support said motor mounting plate on said primary mounting plate in a cantilever fashion;
    a chamber defined by said mounting plates and said supporting means, said chamber being accessible to an operator;
    an ultrasonic test unit insertable into the bore of the rotor;
    a motor mounted on said motor mounting plate to actuate a drive shaft for said test unit; and
    calibration means located in said chamber to calibrate said test unit.

4. An arrangement as claimed in claim 3 wherein said calibrating means comprises a pair of calibrating blocks, a first calibrating block for axial calibration and a second calibrating block for rotational calibration, each of said calibration blocks having a series of holes formed therein at predetermined distances to calibrate and check the operation of said test unit.

5. An arrangement as claimed in claim 4 wherein said calibrating blocks are removably mounted in a frame in said chamber.

6. An arrangement as claimed in claim 1 wherein extensions of said drive shaft may be inserted between said motor and said test unit, said extensions being coupled and uncoupled in said chamber.

7. An arrangement as claimed in claim 2 wherein:
    said motor has a short section of drive shaft extending therefrom;
    said test unit being coupled to said section of drive shaft and having mounting arrangement to mount the test unit in the bore of the rotor;
    said motor mounting plate being pivotable to permit insertion of precisely determined extension lengths of said drive shaft into said chamber between said motor and said test unit to extend the test unit into the bore of the rotor, said extension lengths being coupled and uncoupled in said chamber.

8. An ultrasonic flaw detecting arrangement for turbine rotor bores comprising:

a primary mounting plate secured to the rotor and having a central opening therein permitting access to the bore of the rotor;

a support ring;

supporting rods rigidly supporting said support ring on said primary mounting plate in a cantilever fashion;

a chamber defined by said primary mounting plate, said support ring and said supporting rods;

a motor mounting plate pivotably connected to said support ring so that it can be pivoted to permit easy access to said chamber;

a motor on said motor mounting plate to actuate a short section of drive shaft adapted for rotation in said motor mounting plate;

coupling means to connect said short section of drive shaft to another section of drive shaft;

a test unit in the bore of the rotor rotated by said drive shaft for rotational testing of the bore, said test unit including a movable carriage driven for axial testing of the bore;

a first calibration block to calibrate the axial operation of said test unit removably mounted in said chamber; and a second calibration block to calibrate the rotational operation of said test unit removably mounted in said chamber adjacent said opening in said primary mounting block.

9. An arrangement as claimed in claim 8 wherein said test unit further comprises:

a pair of ultrasonic transducer carrying shoes pneumatically biased against the bore of the rotor;

a second motor to drive said movable carriage in the axial direction; and spider supports at each end of said test unit.

* * * * *